United States Patent [19]

Horvath

[11] Patent Number: 4,958,705

[45] Date of Patent: Sep. 25, 1990

[54] HYDRAULIC CONTROLLER, ESPECIALLY FOR THE MOVEMENT OF A PROSTHETIC JOINT

[75] Inventor: Edward Horvath, Vienna, Austria

[73] Assignee: Otto Bock Orthopädische Industrie Besitz-Und Verwaltungs - KG, Duderstadt, Fed. Rep. of Germany

[21] Appl. No.: 264,213

[22] Filed: Oct. 28, 1988

[30] Foreign Application Priority Data

Oct. 30, 1987 [AT] Austria ..................... 286487

[51] Int. Cl.⁵ ........................... F16F 9/00; A61F 2/00
[52] U.S. Cl. ................................... 188/314; 188/318; 623/26
[58] Field of Search .................... 188/313, 318, 322.15, 188/314, 281, 298, 322.22; 92/8, 52; 623/26, 37, 39; 280/714

[56] References Cited

U.S. PATENT DOCUMENTS 4,051,558 10/1977 Vallotton ........................ 623/26
4,266,639 5/1981 Schloth ........................... 188/314 X

FOREIGN PATENT DOCUMENTS 3327006 2/1984 Fed. Rep. of Germany ........... 92/8
2577415 8/1986 France .
0034809 2/1987 Japan ................................. 188/314
6868185 9/1981 U.S.S.R. ............................. 188/314

*Primary Examiner*—Robert J. Oberleitner
*Attorney, Agent, or Firm*—Herbert Dubno

[57] ABSTRACT

A hydraulic controller for the motion of a prosthetic joint has a piston-and-cylinder unit whose working chambers on opposite sides of the piston are connected to each other by a connecting passage and to a compensating chamber which stores a volume of hydraulic fluid to compensate for the difference in the volumes of the cylinder chambers resulting from the fact that the piston rod passes through one of them. Regardless of the direction of movement of the piston in the cylinder, utilizing checkvalves and adjustable throttle elements, the flow is controlled between the chambers so that separate throttle elements can effectively control the opposite movements while check valves permit filling of chambers.

14 Claims, 2 Drawing Sheets

4,958,705

HYDRAULIC CONTROLLER, ESPECIALLY FOR THE MOVEMENT OF A PROSTHETIC JOINT

CROSS REFERENCE TO RELATED APPLICATIONS

This application is related to the commonly owned copending applications Ser. No. 07/247,896 filed 22 Sept. 1988, now U.S. Pat. No. 4,854,428 and Ser. No. 07/247,897 filed 22 Sept. 1988 and Ser. No. 07/252,859 filed 30 Sept. 1988, now U.S. Pat. No. 4,893,648.

FIELD OF THE INVENTION

My present invention relates to a hydraulic controller and, more particularly, to a hydraulic controller for controlling the movement of an artificial joint, in, for example, a prosthesis in which the hydraulic controller acts to damp or prevent uncontrolled movement of the joint.

BACKGROUND OF THE INVENTION

It is known, in various human prosthetic applications, to provide an artificial joint in which the movement about the axis of the joint or the relative movement of the joint parts is controlled, especially damped, utilizing a piston-and-cylinder unit in which, during one phase of the movement, a piston rod or other piston portion extends further from a cylinder and during the reverse joint movement, the piston rod is forced back into the cylinder, i.e. the unit is contracted.

The piston defines within the cylinder respective cylinder chambers, in which one of the chambers is traversed by the piston rod whereas another chamber, on the opposite side of the piston, is free from this rod. In the present description, the cylinder chamber which is free from the rod may be referred to as the first cylinder chamber whereas the cylinder chamber through which the rod extends can be referred to as the second cylinder chamber.

Generally speaking a passage is provided between the cylinder chambers and includes a control element for the flow between these chambers The two chambers are also connected to a compensation chamber which serves to compensate for the difference in volumes of the cylinder chambers resulting from the presence of the piston rod in one of them. In the passage between the first cylinder chamber and the compensation chamber, a check valve is provided in an arrangement whereby it blocks flow in the direction of the compensation chamber while in the flow path from the first cylinder chamber to the compensation chamber there is also an adjustable throttle element.

In the conventional hydraulic controller of this type, the adjustable throttle element is arranged in the flow path from the first cylinder chamber to the compensation chamber so that, utilizing this adjustable throttle element, it is only possible to control the movement of the piston rod in the direction of retraction of the piston rod or compaction of the piston-and-cylinder unit. The retraction movement of the piston can thus occur with throttled flow through a gap between the second cylinder chamber provided with the piston rod and the compensation chamber and which is generally not controlled or regulated.

The reverse movement or return movement of the piston thus does not allow for control of the piston-and-cylinder unit.

It has been found that a hydraulic controller, especially for the movement of artificial joints in prostheses should have control of the extension of the joint, corresponding to elongation of the piston-and-cylinder unit, in addition to control of the contraction of the unit if the movement of the joint is to most closely approach natural movement.

OBJECTS OF THE INVENTION

It is the principal object of the present invention to provide a hydraulic controller, especially for an artificial joint of a human prosthesis, whereby the drawbacks of earlier hydraulic controllers for this purpose are eliminated.

Another object of the invention is to provide an improved hydraulic controller for the purposes described which allows regulation of the movement of the piston in both directions within the cylinder.

It is also an object of this invention to provide an improved hydraulic controller which can impart a more natural movement to a prosthetic joint, the movement of which is regulated by the hydraulic controller.

SUMMARY OF THE INVENTION

These objects and others which will become apparent hereinafter are attained, in accordance with the present invention in a hydraulic controller, especially for the movement of a prosthetic joint which comprises:

a piston-and-cylinder unit having a cylinder, and a piston displaceable in the cylinder and having a piston rod extending out of one end of the cylinder, the piston defining within the cylinder and on opposite sides of the piston a first cylinder chamber free from the rod and a second cylinder chamber through which the rod extends, the cylinder chambers communicating with one another;

a compensation chamber adapted to receive hydraulic fluid from the first chamber in excess of that required by the second chamber upon displacement of the rod into the cylinder and corresponding to a volume of the rod in the second chamber:

a first check valve communicating between the first chamber and the compensation chamber and oriented to block flow from the first chamber to the compensation chamber but permitting flow from the compensation chamber to the first chamber;

a bypass connected across the first check valve between the first chamber and the compensation chamber and provided with a first throttle element throttling flow cf the fluid therebetween;

means forming a passage connecting the second chamber with the compensation chamber and provided with a further throttle element for throttling flow of the fluid therebetween; and a further check valve connected between at least one of the first and compensation chambers and the second chamber and oriented to block flow of the fluid from the second chamber but permitting flow into the second chamber and filling of the second chamber upon the displacement of the rod.

More specifically, the invention provides a first adjustable throttle element in a bypass passage connected across and around the check valve connected between the first chamber free from the piston rod and the compensation cylinder, while a further adjustable throttle element is provided in the passage between the second cylinder chamber containing the piston rod and the compensation chamber, this second cylinder chamber being also connected to the compensation chamber by a passage or duct provided with a further check valve.

Since this construction provides check valve s between the cylinder chambers and the compensation chamber, the check valves do not affect the flow in their nonblocking directions and permit an obstruction-free filling of the cylinder chambers through the respective check valves as the movement of the piston depressurizes these cylinder chambers selectively. However, in the cylinder chamber in which the hydraulic fluid is pressurized by this movement of the piston, the displaced fluid is forced through the respective adjustable throttle element.

When the unit is extended, i.e. the piston rod moves out of the cylinder, therefore, the fluid displaced from the second cylinder chamber traversed by the piston rod is forced through a further throttle element into the compensation chamber and this movement of the piston is controllable via the adjustment of the further throttle element.

During the contraction movement of the piston into the cylinder, the displaced hydraulic fluid from the first cylinder chamber is pressed through the first adjustable throttle element into the compensation chamber and, depending upon the direction of movement of the piston, the fluid quantity required to fill the cylinder chamber in which the pressure is reduced, can be supplied to that cylinder chamber directly from the compensation chamber via the respective check valve.

Since the return movement as a rule requires a different control than the contraction movement, the first adjustable throttle element in the bypass passage can be set so that it has a different resistance to flow from the resistance to flow of the further adjustable throttle element. In the case of an embodiment in which the main movement direction is the extension of the piston from the cylinder, different types of control can be provided by the two adjustable throttle elements as well.

It has been found to be advantageous to provide a further check valve in a flow passage communicating between the first and second piston. In that case, when the piston displacement corresponds to movement of the piston rod into the cylinder, any part of the hydraulic fluid required to fill the second chamber containing the piston rod can be directly supplied via this passage.

In an especially advantageous variant, the check valve provided between the cylinder chambers can be formed by a changeover valve whose one side is connected to the first cylinder chamber, whose opposite side is connected to the further throttle element and whose port intermediate these two sides is connected to the second cylinder chamber.

This changeover valve makes it possible, upon displacement of the piston into the cylinder, to cut the further adjustable throttle out of the hydraulic fluid path so that all of the surplus displaced fluid is fed via the first adjustable throttle element to the compensation chamber. This permits a completely independent control of the damping effect of the piston-and-cylinder unit in the two directions of movement of the piston in the cylinder.

In order to better match the control effect to the movements of an artificial joint, it has been found to be advantageous to provide the adjustable throttle elements with further throttle elements connected in parallel thereto and closing upon a rise in pressure and yet other throttle elements which open with a still further rise in pressure.

These throttle elements are connected in parallel to one another and with the respective adjustable throttle elements.

By providing throttle elements which close upon a rise in pressure, in spite of the rise in pressure at one side of the piston, the piston movement within the cylinder is not accelerated with this arrangement. This means that there will not be an undesired increase in the movement of the elements of an artificial joint as might be the case in hydraulic control arrangements in which sudden pressure rises are not compensated by the parallel-connected throttles of the present invention. The throttle elements which open with a still further increase in pressure prevent damage to parts of the control system which may be injured by excessive pressures.

The throttle elements which open automatically upon an increase in pressure and close automatically upon an increase in pressure can be biased into their original position by springs.

According to a further feature of the invention, the control element in the connection between the two cylinder chambers can be constituted as a throttle while the further adjustable throttle element is provided with a bypass in which the check valve blocking flow from the second chamber to the compensation chamber is arranged. In this construction, even if there is a nonequal movement characteristic or control effect by the two throttle elements, detectable nonuniform movement characteristics are excluded since the throttle in the passage between the cylinder chambers always allows a certain cross flow of liquid from one side of the piston to the other side of the piston. The check valves between the cylinder chambers and the compensation chamber allow filling of the cylinder chambers behind the piston with respect to the direction of movement thereof in each case, when the aforementioned throttle is provided, without permitting an excessively high, negative pressure to develop in the respective cylinder chamber and without permitting the formation of vapor bubbles in the liquid which might result from such an excessively reduced pressure.

According to another feature of the invention, the further check valve can be provided directly in the connecting duct between the second cylinder chamber and the compensation chamber, the further adjustable throttle element being provided in a bypass across the check valve. In this construction, therefore, all of the liquid displaced passes through a respective throttle element and all of the liquid required to fill the depressurized cylinder chamber is directly drawn from the compensation chamber via the respective check valve.

This also prevents a negative pressure from developing in the depressurized cylinder chamber which can interfere with filling.

This arrangement avoids the need to fill the depressurized cylinder chamber selectively through respective throttle elements which can introduce turbulence to interfere with the filling.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
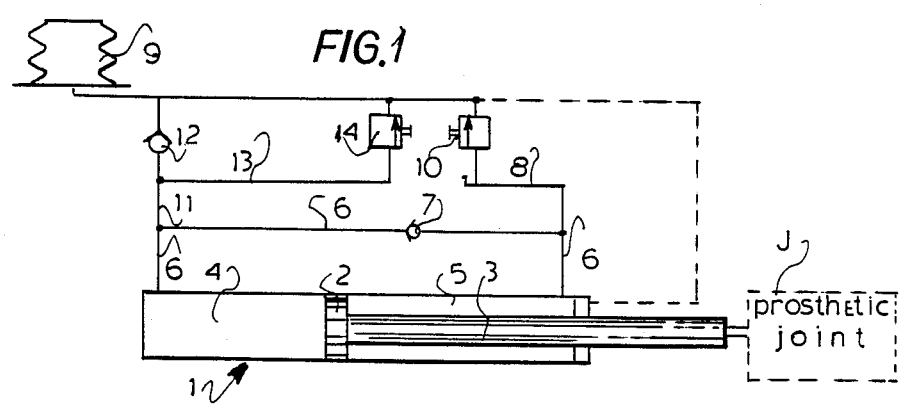
FIG. 1 is a flow diagram illustrating the simplest case of a hydraulic controller according to the invention.

FIG. 1 shows a cylinder 1 in which a piston 2 is displaceable in the axial direction together with its piston rod 3. The unit 1 is connected to the elements of a prosthetic joint represented at J in FIG. 1 and it will be understood that the piston-and-cylinder units of the remaining Figures likewise are connected between the movable elements of a prosthetic joint to regulate the motion in both directions of the joint corresponding to the contraction and elongation of the piston-and-cylinder unit respectively.

The piston 2 defines within the cylinder 1 a first cylinder chamber 4 free from any piston rod and a second cylinder chamber 5 through which the piston rod 3 extends and the volume of which is reduced correspondingly to the volume of the piston rod within this chamber.

From the first chamber to the second chamber a passage 6 extends and this passage can include a first check valve which is so positioned that it will block the flow from the second chamber 5 to the first chamber 4 but will permit hydraulic fluid flow in the opposite direction.

A duct 8 connects the passage 6 to a compensation chamber 9 which serves to receive hydraulic fluid compensating for the difference in the volumes between the cylinder chambers 4 and 5.

In the duct 8 is a further controllable throttle element 10 whose throttle element effect can be adjusted by means of a setting screw shown diagrammatically at 10a but not structurally illustrated.

From the cylinder chamber 4 or the passage 6 communicating therewith, a duct 11 extends to the compensation chamber 9 and includes a further check valve 12 which is positioned to block the direct flow of hydraulic fluid from cylinder chamber 4 into the compensation chamber 9. This further check valve is bypassed by a bypass passage 13 containing a first controllable throttle element 14.

Upon extension movement of the piston 2, 3 to the right, therefore, the fluid displaced from chamber 5 passes only through the throttle element 10 at an adjustable rate to the compensation chamber 9 While there is practically free flow of hydraulic fluid from this compensation chamber via the check valve 12 to the cylinder chamber 4.

Upon the contractile movement of the device, corresponding to movement of the piston 2, 3 to the left, a portion of the hydraulic fluid displaced from chamber 4 passes via the check valve 7 into the chamber 5 while another portion can flow through the bypass 13 to the compensation chamber 9 via the adjustable throttle element 14 which controls movement of the joint corresponding to the contraction of the piston-and-cylinder unit.

Figure 2:
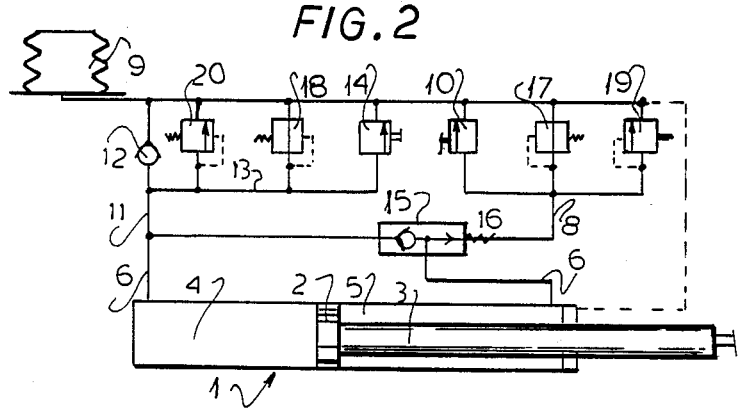
FIG. 2 shows a hydraulic controller in which each of the throttle elements is provided in parallel with a plurality of additional throttle elements.
Figure 3:
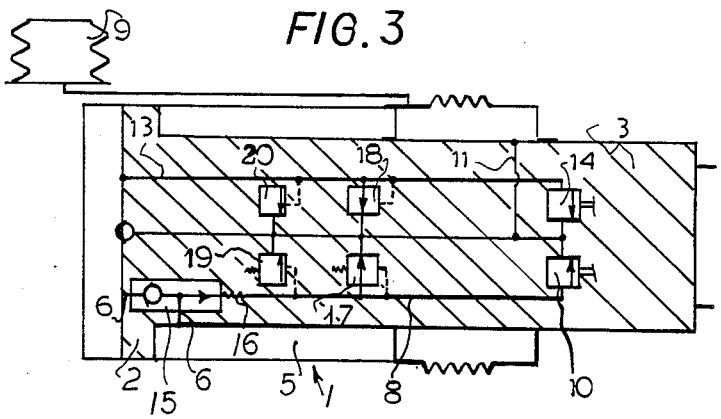
FIG. 3 is a diagram illustrating a compact configuration of the hydraulic controller according to the invention whereby the control elements are provided in the piston and piston rod of the piston-and-cylinder unit.

In the embodiment of the control device illustrated in FIGS. 2 and 3, the first check valve 7 is replaced by a changeover valve 15 which functions as a double-acting check valve.

One end of the connecting passage 6 communicating with the first chamber 4 is connected to one side of the changeover valve 15.

The other side of the changeover valve 15 is connected to the duct 8 which is provided with a further throttle element 10.

An intermediate port of the changeover valve between the seats thereof is connected to the portion of the connection passage 6 communicating with the second cylinder chamber 5.

The changeover valve can be preloaded as represented by the spring 16 in the direction of blocking flow toward the first cylinder chamber 4 so that the outward flow from cylinder chamber 5 to the cylinder chamber 4 is prevented.

Both in the duct 8 and in the bypass 13, parallel to the further controllable throttle element 10 and the first controllable throttle element 14, I provide throttle elements 17 and 18, respectively, which close upon a rise in pressure and throttle elements 19 and 20, respectively, which open upon a further rise in pressure.

In these Figures, therefore, like in the embodiment of FIG. 1, when the piston 2 is drawn by the piston rod 3 to the right, corresponding to extension of the joint, for example, the hydraulic fluid will flow via a portion of the connecting passage 6, the duct 8 and the further controllable throttle element 10 to the compensation chamber 9 at a rate which is controlled by the throttle element 10. Simultaneously, hydraulic fluid is drawn from the compensation chamber 9 via the duct 11 and the check valve 12 to the cylinder chamber 4. Since there is no throttling in the duct 11, the movement in this direction is controlled exclusively by the further control-throttle element 10.

If the piston 2 is moved in the cylinder 1 to the left, hydraulic fluid is forced from the cylinder chamber 4 through the connecting passage 6 and the check valve 7 in part to the cylinder chamber 5 whereby the excess fluid according to the volume difference as in the case of the embodiment of FIG. 1, corresponding to the difference in volumes between cylinder chambers, is fed to the compensation chamber 9 via the passage 8 and the adjustable throttle element. If the latter throttle element contributes a smaller resistance to flow, it will control the rate at which the piston will move by regulating primarily the rate at which the excess fluid is delivered to the compensation chamber 9.

In the embodiment of FIGS. 2 and 3, the hydraulic fluid from the chamber 4 is delivered to the chamber 5 in part through the changeover valve 15, the valve member of this changeover valve blocking flow to the duct 8 and the throttle elements 10, 17 and 19. Only the throttled flow through the controllable throttle element 14 and the pressure responsive throttle elements 18 and 20 then governs the displacement of the piston 3.

In the embodiments of FIGS. 2 and 3, an increase in pressure above the predetermined level will result in closure of the throttle elements 17 or 18 in the duct 8 or in the bypass 13 so that the piston movement which might have been excessively rapid to cause the pressure increase, will be slowed by the increased throttling effect.

Upon a further increase in the pressure in duct 8 or the bypass 13, the valve 19 or 20 will open to prevent blockage of the joint by an excessively high counterpressure and improving the reliability of the joint operation. The throttle elements 17-20 are biased by respective springs into their respective starting positions when the pressures in the duct 8 and bypass 13 return to their normal values.

FIG. 3 has been provided to show symbolically that many of the key elements including the throttle elements and check valves can be provided directly in the piston or rod.

Figure 4:
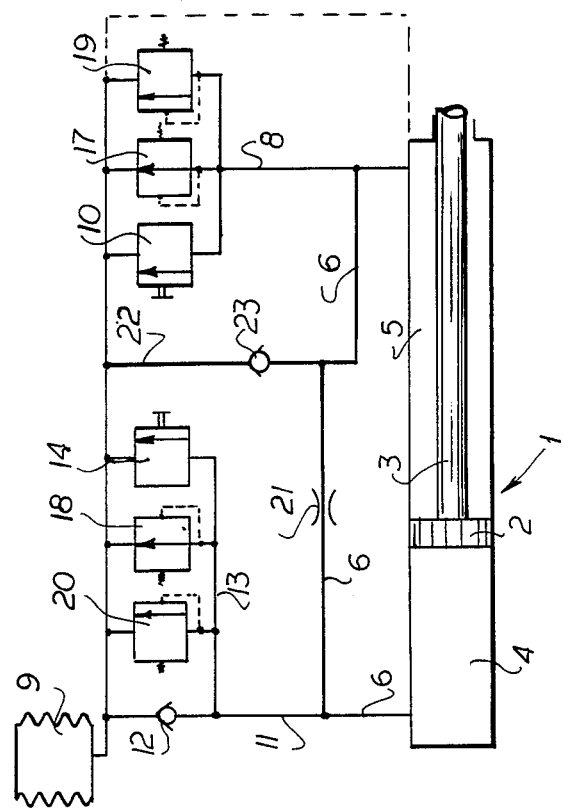
FIG. 4 is a flow diagram illustrating a further embodiment of the invention somewhat analogous to that of FIG. 2.

In the embodiment of FIG. 4, in the connecting passage 6 between the cylinder chambers 4 and 5, a throttle 21 of a predetermined flow cross section is provided In this embodiment, therefore, the direct connection between the two cylinder chambers does not have a check valve. Rather across the further adjustable throttle element 10 I provide a bypass duct 22 in which a check valve 23 is located to block the flow of hydraulic fluid from the cylinder 5 to the compensation chamber 9.

If the piston 2 is shifted in the direction of extension of the piston-and-cylinder unit, i.e. to the right, the hydraulic fluid displaced from the cylinder chamber 5 in FIG. 4, when the flow resistance in the throttle 21 is greater than that of the controllable throttle element 10, passes via this throttle element 10 to the compensation chamber.

Concurrently hydraulic fluid from the compensation chamber flows through the open check valve 12 and duct 11 and a part of duct 6 to be sucked into the chamber 4. As a result, there is a damping of the movement through the adjustable throttle element 10.

Should the flow resistance of the throttle element 10 be greater than that of throttle 21, the fluid forced out of cylinder chamber 5 will pass via the throttle 4 into the cylinder chamber 21 so that the compensation chamber 9 will contribute to the cylinder chamber 4 only the volume difference required for filling the latter via the check valve 12.

Upon displacement of the piston 2 in the opposite direction namely to the left in FIG. 4, the direction in which the piston rod is retracted into the cylinder, the hydraulic fluid volume required for filling the cylinder chamber 5 is drawn either through the throttle 21 or through the adjustable throttle element 10 or via the bypass 22 and the check valve 23, depending upon the relative flow resistances.

The volume difference between the fluid volume displaced from the chamber 4 and that required to fill the chamber 5 is taken up by the compensation chamber via the throttle element 14.

The throttle 21 in any case ensures that there will be a flow from cylinder chamber to cylinder chamber with a damping effect in both directions, although the control of the damping characteristics in the two directions can be effected by differently adjusting the throttle elements 10 and 14. Abrupt transitions in the control characteristic upon the transition from an inward movement to an outward movement and vice versa can thus be avoided.

Figure 5:
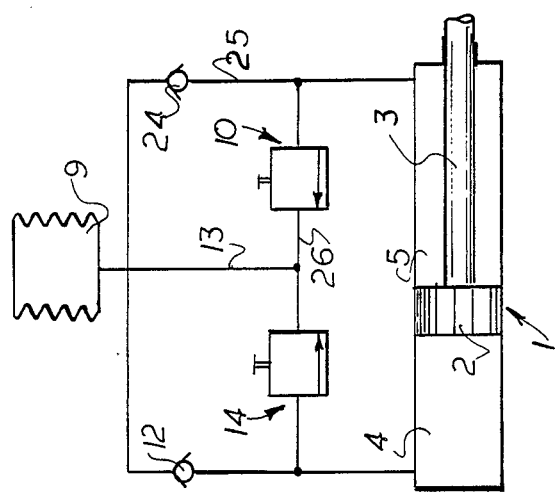
FIG. 5 is a flow diagram of another very simple embodiment of the invention.

The embodiment of FIG. 5 has an especially simple construction in that the further check valve 24 is provided directly in the connecting passage 25 between the second cylinder chamber 5 and the compensation chamber 9 The further adjustable throttle element 10 is provided in a bypass 26 across the check valve 24.

If the piston 2 in FIG. 5 is shifted to the left, i.e. further into the cylinder, the hydraulic fluid displaced from the cylinder chamber 4 is forced through the first adjustable throttle element 14 and duct 13 into the compensation chamber 9 since the other flow passage is blocked via the check valve 12. The filling of the cylinder chamber behind the piston, i.e. cylinder chamber 5 is effected without interference through the open check valve 24 and duct 25, from the compensation chamber 9.

When the piston is drawn to the right and its rod extended from the cylinder, the hydraulic fluid forced from the cylinder chamber 5 is displaced via duct 26 and the further adjustable throttle element 10 into the compensation chamber and filling of the cylinder chamber 4 is effected through the open throttle 12 and its duct which does not have any further control valve therein which could detrimentally effect such filling.

I claim:

1. A hydraulic controller, especially for the movement of a prosthetic joint, comprising:
   a piston-and-cylinder unit having a cylinder, and a piston displaceable in said cylinder and having a piston rod extending ut of one end of said cylinder, said piston defining within said cylinder and on opposite sides of said piston a first cylinder chamber free from said rod and a second cylinder chamber through which said rod extends, said cylinder chambers communicating with one another;
   a compensation chamber adapted to receive hydraulic fluid from said first chamber in excess of that required by said second chamber upon displacement of said rod into said cylinder and corresponding to a volume of said rod in said second chamber;
   a first check valve communicating between said first chamber and said compensation chamber and oriented to block flow from said first chamber to said compensation chamber but permitting flow from said compensation chamber to said first chamber;
   a bypass connected across said first check valve between said first chamber and said compensation chamber and provided with a first throttle element throttling flow of said fluid therebetween;
   means forming a passage connecting said second chamber with said compensation chamber and provided with a further throttle element for throttling flow of said fluid therebetween; and
   a further check valve connected between at least one of said first and compensation chambers and said second chamber and oriented to block flow of said fluid from said second chamber but permitting flow into said second chamber and filling of said second chamber upon said displacement of said rod, said further check valve being provided in a flow passage communicating between said first and second chambers and connected to said first and second chambers between said throttle elements and first and second said chambers, respectively, said check valves and throttle elements being provided directly in said piston and said rod.

2. A hydraulic controller, especially for the movement of a prosthetic joint, comprising:
   a piston-and-cylinder unit having a cylinder, and a piston displaceable in said cylinder and having a piston rod extending out of one end of said cylinder, said piston defining within said cylinder and on opposite sides of said piston a first cylinder chamber free from said rod and a second cylinder chamber through which said rod extends, said cylinder chambers communicating with one another;

a compensation chamber adapted to receive hydraulic fluid from said first chamber in excess of that required by said second chamber upon displacement of said rod into said cylinder and corresponding to a volume of said rod in said second chamber;

a first check valve communicating between said first chamber and said compensation chamber and oriented to block flow from said first chamber to said compensation chamber but permitting flow from said compensation chamber to said first chamber;

a bypass connected across said first check valve between said first chamber and said compensation chamber and provided with a first throttle element throttling flow of said fluid therebetween;

means forming a passage connecting said second chamber with said compensation chamber and provided with a further throttle element for throttling flow of said fluid therebetween; and a further check valve connected between at least one of said first and compensation chambers and said second chamber and oriented to block flow of said fluid from said second chamber but permitting flow into said second chamber and filling of said second chamber upon said displacement of said rod, said further check valve being provided in a flow passage communicating between said first and second chambers, said further check valve being a changeover valve having one side connected to said first chamber and to said bypass, an opposite side connected to said further throttle element, and a port between said sides of said changeover valve connected to said second chamber.

3. A hydraulic controller, especially for the movement of a prosthetic joint, comprising:

a piston-and-cylinder unit having a cylinder, and a piston displaceable in said cylinder and having a piston rod extending out of one end of said cylinder, said piston defining within said cylinder and on opposite sides of said piston a first cylinder chamber free from said rod and a second cylinder chamber through which said rod extends, said cylinder chambers communicating with one another;

a compensation chamber adapted to receive hydraulic fluid from said first chamber in excess of that required by said second chamber upon displacement of said rod into said cylinder and corresponding to a volume of said rod in said second chamber;

a first check valve communicating between said first chamber and said compensation chamber and oriented to block flow from said first chamber to said compensation chamber but permitting flow from said compensation chamber to said first chamber;

a bypass connected across said first check valve between said first chamber and said compensation chamber and provided with a first throttle element throttling flow of said fluid therebetween;

means forming a passage connecting said second chamber with said compensation chamber and provided with a further throttle element for throttling flow of said fluid therebetween;

a further check valve connected between at least one of said first and compensation chambers and said second chamber and oriented to block flow of said fluid from said second chamber but permitting flow into said second chamber and filling of said second chamber upon said displacement of said rod; and at least one pressure-controlled throttle element connected in parallel to and cross one of said first and further throttle elements and closing upon an increase in pressure.

4. The hydraulic controller defined in claim 3, further comprising at least one additional pressure-controlled throttle element connected in parallel to and across said one of said first and further throttle elements and opening upon a still-further increase in pressure.

5. The hydraulic controller defined in claim 4, wherein said additional pressure-controlled throttle element is spring-loaded for resetting to a normally closed position.

6. A hydraulic controller, especially for the movement of a prosthetic joint, comprising:

a piston-and-cylinder unit having a cylinder, and a piston displaceable in said cylinder and having a piston rod extending out of one end of said cylinder, said piston defining within said cylinder and on opposite sides of said piston a first cylinder chamber free from said rod and a second cylinder chamber through which said rod extends, said cylinder chambers communicating with one another;

a compensation chamber adapted to receive hydraulic fluid from said first chamber in excess of that required by said second chamber upon displacement of said rod into said cylinder and corresponding to a volume of said rod in said second chamber;

a first check valve communicating between said first chamber and said compensation chamber and oriented to block flow from said first chamber to said compensation chamber but permitting flow from said compensation chamber to said first chamber;

a bypass connected across said first check valve between said first chamber an said compensation chamber and provided with a first throttle element throttling flow of said fluid therebetween;

means forming a passage connecting said second chamber with said compensating chamber and provided with a further throttle element for throttling flow of said fluid therebetween;

a further check valve connected between at least one of said first and compensation chambers and said second chamber and oriented to block flow of said fluid from said second chamber but permitting flow into said second chamber and filling of said second chamber upon said displacement of said rod; and at least one pressure-controlled throttle element connected in parallel to and across each of said first and further throttle elements and closing upon an increase in pressure.

7. The hydraulic controller defined in claim 6, further comprising at least one additional pressure-controlled throttle element connected in parallel to and across said each of said first and further throttle elements and opening upon a still-further increase in pressure.

8. The hydraulic controller defined in claim 7 wherein each of said additional pressure-controlled throttle elements is spring-loaded for resetting to a normally closed position.

9. A hydraulic controller, especially for the movement of a prosthetic joint, comprising:

a piston-and-cylinder unit having a cylinder, and a piston displaceable in said cylinder and having a piston rod extending out of one end of said cylinder, said piston defining within said cylinder and on opposite sides of said piston a first cylinder chamber free from said rod and a second cylinder chamber through which said rod extends, said cylinder chambers communicating with one another;

a compensation chamber adapted to receive hydraulic fluid from said first chamber in excess of that required by said second chamber upon displacement of said rod into said cylinder and corresponding to a volume of said rod in said second chamber;

a first check valve communicating between said first chamber and said compensation chamber and oriented to block flow from said first chamber to said compensation chamber but permitting flow from said compensation chamber to said first chamber;

a bypass connected across said first check valve between said first chamber and said compensation chamber and provided with a first throttle element throttling flow of said fluid therebetween;

means forming a passage connecting said second chamber with said compensation chamber and provided with a further throttle element for throttling flow of said fluid therebetween;

a further check valve connected between at least one of said first and compensation chambers and said second chamber and oriented to block flow of said fluid from said second chamber but permitting flow into said second chamber and filling of said second chamber upon said displacement of said rod; and at least one additional pressure-controlled throttle element connected in parallel to and across at least one of said first and further throttle elements and opening upon an increase in pressure supplied thereto.

10. The hydraulic controller defined in claim 8 wherein said additional pressure-controlled throttle element is spring-loaded for resetting to a normally closed position.

11. The hydraulic controller defined in claim 10, further comprising at least one additional pressure-controlled-throttle element connected in parallel to and across at least each of said first and further throttle elements and opening upon an increase in pressure supplied thereto.

12. The hydraulic controller defined in claim 11 wherein each of said additional pressure-controlled throttle elements is spring-loaded for resetting to a normally closed position.

13. A hydraulic controller, especially for the movement of a prosthetic joint, comprising:

a piston-and-cylinder unit having a cylinder, and a piston displaceable in said cylinder and having a piston rod extending out of one end of said cylinder, said piston defining within said cylinder and on opposite sides of said piston a first cylinder chamber free from said rod and a second cylinder chamber through which said rod extends, said cylinder chambers communicating with one another;

a compensation chamber adapted to receive hydraulic fluid from said first chamber in excess of that required by said second chamber upon displacement of said rod into said cylinder and corresponding to a volume of said rod in said second chamber;

a first check valve communicating between said first chamber and said compensation chamber and oriented to block flow from said first chamber to said compensation chamber but permitting flow from said compensation chamber to said first chamber;

a bypass connected across said first check valve between said first chamber and said compensation chamber and provided with a first throttle element throttling flow of said fluid therebetween;

means forming a passage connecting said second chamber with said compensation chamber and provided with a further throttle element for throttling flow of said fluid therebetween; and a further check valve connected between at least one of said first and compensation chambers and said second chamber and oriented to block flow of said fluid from said second chamber but permitting flow into said second chamber and filling of said second chamber upon said displacement of said rod, a throttle communicating between said first and second chambers and another bypass is connected across said further throttle element and is provided with said further check valve which blocks flow from said second chamber to said compensation chamber.

14. A hydraulic controller, especially for the movement of a prosthetic joint, comprising:

a piston-and-cylinder unit having a cylinder, and a piston displaceable in said cylinder and having a piston rod extending out of one end of said cylinder, said piston defining within said cylinder and on opposite sides of said piston a first cylinder chamber free from said rod and a second cylinder chamber through which said rod extends, said cylinder chambers communicating with one another;

a compensation chamber adapted to receive hydraulic fluid from said first chamber in excess of that required by said second chamber upon displacement of said rod into said cylinder and corresponding to a volume of said rod in said second chamber;

a first check valve communicating between said first chamber an said compensation chamber and oriented to block flow from said first chamber to said compensation chamber but permitting flow from said compensation chamber to said first chamber;

a bypass connected across said first check valve between said first chamber and said compensation chamber and provided with a first throttle element throttling flow of said fluid therebetween;

means forming a passage connecting said second chamber with said compensation chamber and provided with a further throttle element for throttling flow of said fluid therebetween; and a further check valve connected between at least one of said first and compensation chambers and said second chamber and oriented to block flow of said fluid from said second chamber but permitting flow into said second chamber and filling of said second chamber upon said displacement of said rod, said further check valve being provided directly in a passage between said second chamber and the compensation chamber and said further throttle element is located in a further bypass connected across said further check valve.

* * * * *